(12) United States Patent
Prasad et al.

US006514481B1

(10) Patent No.: US 6,514,481 B1
(45) Date of Patent: Feb. 4, 2003

(54) MAGNETIC NANOPARTICLES FOR SELECTIVE THERAPY

(75) Inventors: Paras N. Prasad, Williamsville, NY (US); Earl J. Bergey, South Dayton, NY (US); Charles Liebow, East Amherst, NY (US); Laurent Levy, Paris (FR)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/718,825

(22) Filed: Nov. 22, 2000

Related U.S. Application Data (60) Provisional application No. 60/166,777, filed on Nov. 22, 1999.

(51) Int. Cl.[7] .................. A61B 5/055; A61K 9/16; B32B 5/16
(52) U.S. Cl. ............... 424/9.32; 424/490; 424/486; 424/646; 424/617; 530/399; 436/173; 427/128; 427/130; 324/307; 324/309
(58) Field of Search ................ 424/9.32, 490, 424/646, 617, 486; 530/399; 324/307, 309; 427/128, 130; 436/173

(56) References Cited

U.S. PATENT DOCUMENTS

| | | |
|---|---|---|
| 5,427,767 A | 6/1995 | Kresse et al. |
| 5,460,830 A | 10/1995 | Kossovsky et al. |
| 5,460,831 A | 10/1995 | Kossovsky et al. |
| 5,593,740 A | 1/1997 | Strumban et al. |
| 6,045,925 A | 4/2000 | Klabunde et al. |
| 6,048,515 A | 4/2000 | Kresse et al. |

OTHER PUBLICATIONS

Schally, et al, Cancer Chemotherapy Based on Targeting of Cytotoxic Peptide Conjugates to Their Receptors on Tumors Eur. J. of Endocinology, 1999, 141 p. 1–14.

Nagy, et al, Cytotoxic Analogs of Luteinizing Hormone–Releasing Hormone Containing Doxorubicin or 2–Pyrrolino–doxorubicin, a Derivative 500–1000 Times More Potent Proc. Natl. Acad. Sci. USA, Jul. 1996, vol. 93, pp. 7269–7273.

Emons, et al, High Affinity Binding and Direct Antiproliferative Effects of Luteinizing Hormone–Releasing Hormone Analogs in Human Endometrial Cancer Cell Lines J. Clinical Endocinology and Metabolism, 1993, pp. 1458–1464.

Schiitt et al, Applications of Magnetic Targeting in Diagnosis and Therapy—Possibilities and Limitations: A Mini–Review, Hybridoma Nov. 1, 1997, vol. 16, pp. 109–117.

Hilger, et al, Evaluation of Temperature Increase With Different Amounts of Magnetite in Liver Tissue Samples, Investigative Radiology Nov. 11, 1997, vol. 32, pp 705–712.

*Primary Examiner*—Karen Cochrane Carlson
*Assistant Examiner*—Chih-Min Kam
(74) *Attorney, Agent, or Firm*—Hodgson Russ LLP (57) ABSTRACT

The present invention provides novel nanosized particles termed as "nanoclinics" for therapeutic and/or diagnostic use. The particles have a core made of a therapeutic or diagnostic material surrounded by a shell. Further, the particles contain a targeting agent on the surface of the shell for specific recognition of targeted cells. A method is also provided for lysis of cells using DC magnetic field. Further, the present invention also provides a method for fabrication of nanoclinics that can target and lyse specific cells such as cancer cells.

21 Claims, 6 Drawing Sheets

MAGNETIC NANOPARTICLES FOR SELECTIVE THERAPY

This application claims priority of U.S. provisional patent application No. 60/166,777 filed on Nov. 22, 1999, the disclosure of which is incorporated herein by reference.

FIELD OF INVENTION

The present invention relates generally to the area of delivery of materials, for intracellular therapeutics or diagnosis. More particularly, the present invention provides magnetic nanoparticles, a method for making the particles, and a method for using the particles in the treatment of cancer using a DC magnetic field.

BACKGROUND OF THE INVENTION

In the past 30 years, major advances have been made in the diagnosis and treatment of human malignancies. In parallel, biotechnologies and nanotechnologies have provided avenues for the development of novel approaches to treatment of human diseases. Currently, chemotherapy is a widely used method of treatment for many cancers, but it has some distinct limitations and disadvantages. The main disadvantage of chemotherapy is related to drug toxicity, which severely restricts the drug dosages that can be used to effect eradication of the cancerous cells. To provide a more effective chemotherapeutic approach, one area of research has focused on specific targeting of chemotherapeutic objects to the cancer cells (Schally et al., 1999, *J. Endocrinol.*, 141:1; Nagy et al., 1996, *Proc. Natl. Acad. Sci., USA*, 93:7269; Emons et al., 1993, *J. Clin. Endocrinol. Metab.*, 77:1458). Thus, cancerous cells may be targeted based on district molecules on the cells surface.

Since 1950, magnetic probes and particles have been investigated as a potential treatment for cancer. Studies demonstrate that the hyperthermia (Grittner et al., 1997, *Hybridoma*, 16:109; Higler et al., 1997, *Invest. Radiol.*, 32:705) generated by magnetic particles coupled to a high frequency AC magnetic field (requiring a tremendous power) could be used as an alternate or an adjuvant to therapy for cancer treatment. The hyperthermic activity (heat produced by the relaxation magnetic energy of the magnetic material) was shown to effectively destroy tumor tissue surrounding the probes or particles. The development of ultra-small magnetic particles (ferrofluids) with high crystallinity provided the next step in magnetically induced hyperthermic therapy. This treatment resulted in reduction of tumor size when the particles are directly injected into the tissue. However, no specificity was shown using such therapy. Thus, there is an ongoing need to develop specific targeting of magnetic nanoproducts.

SUMMARY OF THE INVENTION

The present invention provides novel nanosized (less than 100 nm) particles termed as "nanoclinics" or "nanoparticles" or "nanobubbles" for therapeutic or diagnostic use. The particles have a core of a therapeutic or diagnostic material surrounded by a shell composed of a bio-compatible material. Further, the nanoparticles contain a targeting agent on the surface of the shell for specific recognition of targeted cells. The nanoparticles optionally contain a tracking agent.

The present invention also provides a method for the selective destruction of targeted cells, such as cancerous cells. Upon exposure of the cells to nanoclinics having a magnetic core, cells containing molecules having specific affinity for the targeting agent will attach and/or internalize the nanoclinics. Subsequent application of a DC magnetic field can specifically destroy the targeted cells.

The present invention also provides a method for the preparation of the nanoparticles. The method comprises the steps of forming iron oxide core, forming a silica shell around the iron oxide core and attaching one or more targeting agents to the shell via carbon spacers. A tracking dye may be attached to the iron oxide core so as to be able to track the nanoparticles.

BRIEF DESCRIPTION OF THE DRAWINGS

FIGS. 4A, 4B and 4C are representations of the selectivity and the effect of various conditions on the magnetocytolysis of cells. FIG. 4A indicates the effect of incubation of cells with Silica-nanoclinics, silica-nanoclinics with spacers only and silica-nanoclinics with spacer and LHRH. FIG. 4B represents the effect of time of incubation with silica nanoclinics having spacer and LHRH on magnetocytolysis of MCF-7 cells. FIG. 4C indicates the effect of upregulation or downregulation of LHRH receptors on magnetocytolysis by LHRH-nanoclinics.

DETAILED DESCRIPTION OF THE INVENTION

The terms "nanobubble", "nanoparticle", "nonoclinic" or plurals thereof, are used interchangeably and, for the purposes of the specification, mean, a particle or particles of less than 100 nm diameter having a central core of therapeutic or diagnostic material, a shell surrounding the central core, one or more targeting agents on the surface of the shell; and optionally, a tracking agent.

The term "affinity molecule" means, for the purpose of specification, a molecule on the surface of a targeted cell having a specific affinity for the targeting molecule on the surface of a nanoparticle.

Figure 1:
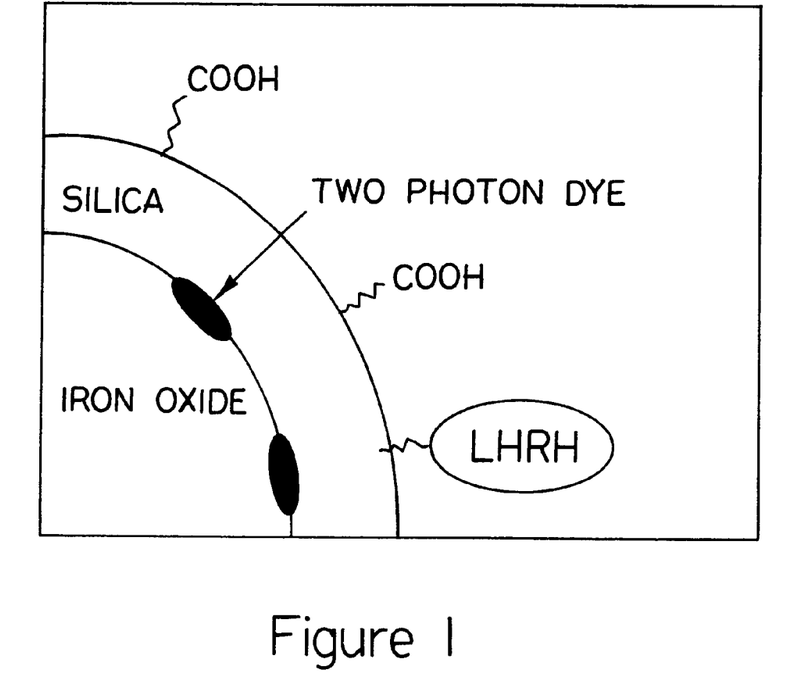
FIG. 1 is a schematic representation of a multifunction nanoclinic. In this illustration, a two-photon dye (ASPI-SH) coated iron oxide core is encapsulated in silica. On the surface, the targeting agent ((D-Lys)$^6$ LH-RH) is attached via a spacer.

A schematic diagram of a nanoparticle of the present invention is shown in FIG. 1. The therapeutic agent in this illustration is iron oxide encapsulated in a silica shell. The nanoparticle shown in this illustration also contains a two photon dye, which acts as a tracking agent. On the surface of the silica shell are present targeting agents, which may be coupled to the shell through spacers so as to prevent steric hindrance during the interaction of the targeting agent with its affinity molecule on cells.

The particles useful for the present invention need to be small enough in size to be able to diffuse into the tissue to enter the cells (by endocytotic processes) and large enough to respond to the applied magnetic field at 37° C. Thus, particles less than 100 nm in diameter, preferably in the range of 5 to 40 nm are suitable for the present invention. The material forming the core may be one or more therapeutic or diagnostic agents. In a preferred embodiment, the therapeutic agent forming the core is a magnetic material. Such materials include ferrous oxide and ferric oxide.

The shell can be made of a bio-compatible material, preferably, silica.

The targeting agent may be any molecule that has specific affinity for a molecule on the surface of the targeted cell. Thus, the targeting agent includes, but is not limited to, antibodies, hormones, or fragments thereof.

The spacer should be long enough to prevent or reduce steric hindrance between the interaction of the targeting agent and the target molecule on the surface of a cell. Carbon spacers are commonly available (such as from Sigma-Aldrich). Suitable spacers contain between 6 and 20 carbon atoms. In a preferred embodiment, the spacer contains 14 carbon atoms.

A tracking agent (also referred to herein as "tracking dye") may be used optionally to track the nanoparticles. The tracking dye may be any fluorescent dye. An example is a dye that has an excitation wavelength in the infra red range. A description of two photon dyes that are suitable is found in U.S. Pat. No. 5,912,247.

In one embodiment, the nanoparticle are multilayered structures comprising an iron oxide core, a two-photon optical probe as the tracking agent, a silica shell and LHRH covalently coupled to the surface of the silica shell. A preferable size for the magnetic core is 20 nm. It is considered that the silica shell stabilizes the magnetic core. Killing of cells that have specific receptors for LHRH is effected by the use of a DC magnetic field such as in a standard MRI system.

The nanoparticles are prepared from iron oxide particles. These particles can be synthesized using a reverse micelle colloidal reaction. After the synthesis of $Fe_2O_3$ particles, a multi-step synthetic process is used to fabricate the nanoparticles. A tracking agent such as a two photon dye (ASPI-SH) can be attached to the surface of the iron oxide particles by bonding the thiol group to the surface metallic atoms thus providing the ability to track the nanoparticles using two-photon laser scanning microscopy. Silica (sodium salt) is added to preform the silica shell. Further silica shell can be grown by TEOS hydrolysis. A carbon spacer is then attached to the silica surface. The spacer reduces the steric hindrance for the binding of the targeting agent to its target molecule. A targeting molecule is then attached to the spacer by standard methods. Alternatively, the targeting agent can be first attached to a spacer and then the targeting agent-spacer complex can be attached to the silica shell.

The porosity of the silica shell can be adjusted by standard methods to select the desired release rate of the therapeutic agent. In addition, a thermostated oil bath can be utilized to increase or reduce the size polydispersity.

The nanoparticles of the present invention can be used for lysis of cells, such as in the treatment of cancer. For the lysis of tumor cells, the targeting agent is selected based on the molecules on the surface of the tumor cells. For example, many tumors express LH-RH receptors. Accordingly, for the lysis of cells of such tumors, nanoclinics of the present invention having LHRH (or a receptor binding analog) can be used as the targeting agent. Human malignancies that are known to express LHRH receptors include, but are not limited to, breast cancer, ovarian cancer, endometrial cancer, prostate cancer, pancreatic cancer. For effecting lysis, tumor cells are exposed to the nanoparticles. Following binding and/or internalization of the nanoparticles by the tumor cells, the patients are exposed to a DC magnetic field. A suitable DC magnetic field is available in standard Magnetic Resonance Imaging equipment which typically has a magnetic filed in the range of 0.1 to 5 Tesla.

The invention will be appreciated better from the following examples, which are intended to be illustrative and not limiting.

EXAMPLE 1

This embodiment describes the preparation of the nanoclinics. An illustrative method for the preparation of nanoparticles, containing a two photon dye as a tracking agent, and LHRH as the targeting agent, is provided.

In 15 ml of water 35 mg of $Fe(DS)_2$ was dispersed (functionalized surfactant: iron dodecyl sulfate). Two hundred microliter of $NH_4OH$ (0.1M) was added following stabilization of temperature to about 80° C. To adjust the size, temperature and $Fe(DS)_2$ concentration can be modified. After about 3 hours of vigorous stirring, iron oxide particles are formed. The solution was cooled down to about 45° C. The two photons dye, ASPI-SH, dispersed in alcohol was directly added to the solution (1 ml of 0.2 M). In order to maximize the bounding between thiol group and iron oxide particles the solution was kept at room temperature for a few hours (4 hrs) under vigorous stirring. To preform the silica layer and prevent aggregation due to strong magnetic interaction, sodium silicate is added to the solution (5 μl per 10 ml of solution). This last step requires several hours (such as 24 hours under stirring and occasional utilization of ultrasonic bath (5 minutes every 4 hours approximately)). The particles were extracted from the colloidal system by several washing and centrifugation (washed with ⅔ water ⅓ alcohol at PH=8.5 to 9). Washed particles were redispersed in a solution (20 ml ethanol and 5 ml water) before addition of base (200 μl of $NH_4OH$ 0.1M) and twenty to 200 μl of tetraethylorthosilicate (TEOS). After about 14 hours, particles are again washed as described above. Spacer molecule, 3-(Triethoxylsilanylpropylcarbamoyl)-Butyric acid, was synthesized (also available commercially) by using 3-(Triethoxylsilyl)propyl amine (4.5 mmol) and 513 mg (4.5 mmol) glutaric anhydride to 1 ml anhydrous DMF. Then 350 μl of di-isopropyl amine was added to the solution drop wise and the mixture is stirred for 24 hours, under argon. Spacer molecule was dispersed in DMF (0.5 g in 20 ml) and 40 mg of particles were added. After 24 h of stirring at room temperature particles were washed with DMF and dried. 2 mg spacer-nanoparticles were dispersed in 1 ml anhydrous DMF using sonication bath. 2 mg of the analog of the peptide hormone LHRH ((D-Lys$_6$) LH-RH) and 24 mg BOP were added. Then, 100 ul DIPEA was added dropwise to the solution. The reaction mixture was sonicated at room temperature for 5 hours. The product is collected by centrifugation (14,000 rpm) and washed with DMF and water. For better stability, the particles were dispersed in a large volume of water with 10% DMSO and concentrated when needed for use.

Using this synthetic protocol, nanoparticles with a tunable size from 5 to 40 nm in diameter can be produced.

EXAMPLE 2

Figure 2:
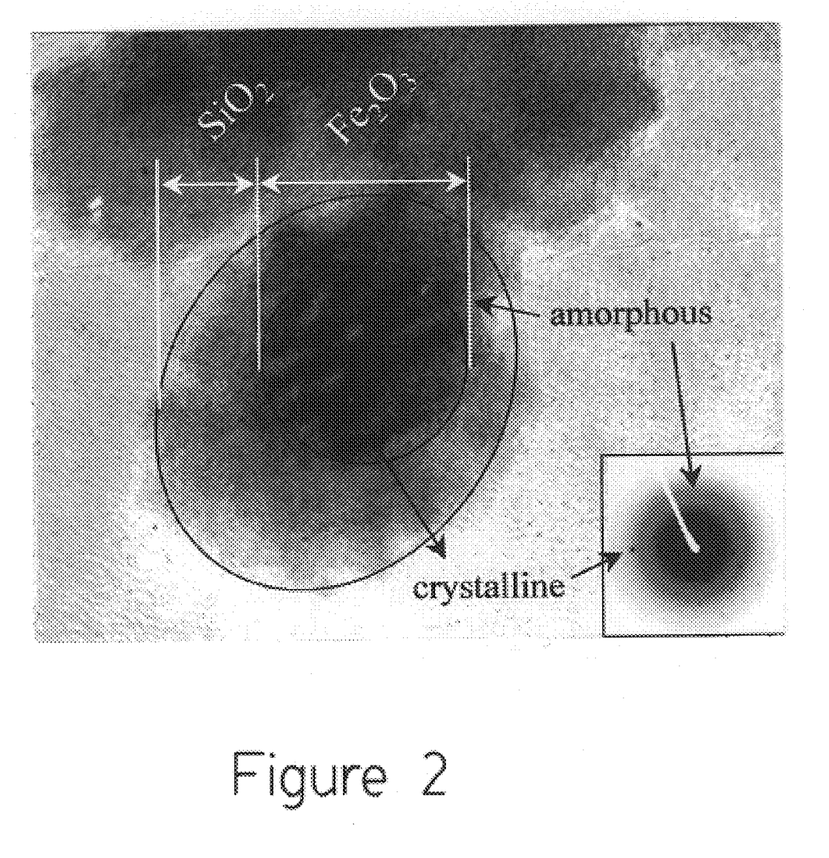
FIG. 2 is a high resolution Transmission Electron Micrograph and electron diffraction profile of a single nanoclinic indicating the presence of amorphous (silica) and crystalline structure (Iron oxide).

This embodiment demonstrates that the nanoparticles prepared by the above method have a core and a shell. The structure of nanoparticles prepared by the method described above was determined by high resolution TEM. High resolution transmission electron microscopy (FIG. 2A) shows the structure of the nanoparticle is composed of the crystalline core corresponding to $Fe_2O_3$ and one amorphous silica layer (bubble). The same crystalline/amorphous structure was obtained by the electron diffraction (insert FIG. 2A) of the particle and also confirmed by X-ray diffraction.

EXAMPLE 3

Figure 3:
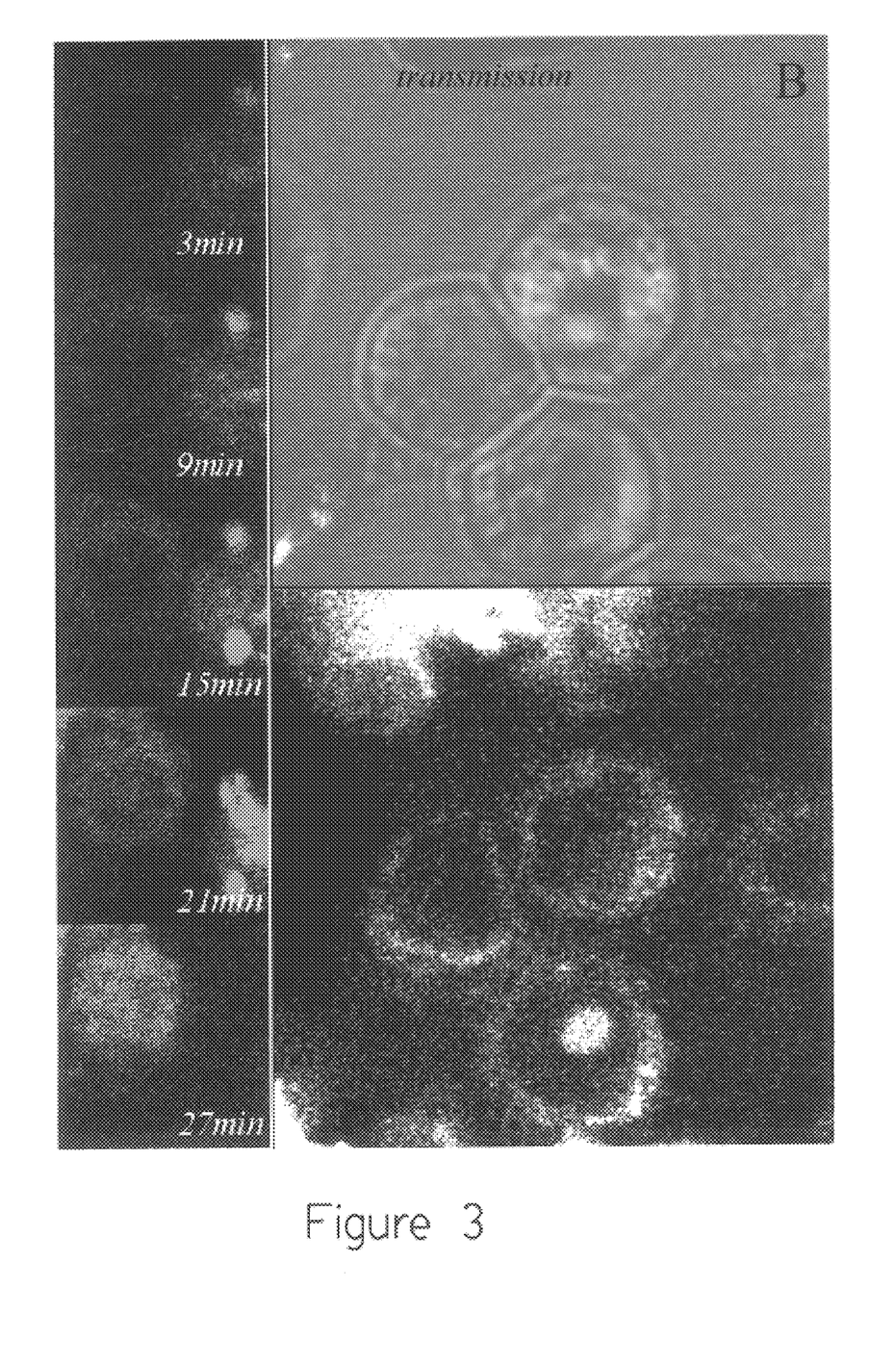
FIG. 3 is a representation of Laser scanning microscopy showing uptake of nanoclinics by epithelial oral cancer cells (KB cells). Images show uptake as indicated by the tracking dye after 3, 9, 15, 21 and 27 minutes incubation (A). (B) is a representation of the transmission photomicrograph and (C) is a representation of the corresponding luminescence photo micrograph.

This embodiment demonstrates that the nanoparticles as prepared in Example 1 can be used for selective uptake by targeted cells. The selective interaction and internalization of these nanoparticles with cells was visualized using two photon laser scanning microscopy. The two-photon dye is able to absorb one photon (with energy of 400 nm) or two photons (with 800 nm energy) via a virtual state. Using near-infrared light (800 nm), cells were observed by real time tracking. Two different types of particles were used in this study, LHRH-positive (surface coupled) and LHRH-negative (C14 spacer arm only). Oral Epithelial carcinoma (KB) cells were used to determine the effect of the nanoparticles. These cells are known to be LHRH receptor positive. A suspension of nanoparticles was added to the cells and uptake was observed using laser scanning microscopy. Two-photon Laser scanning microscopy was performed using a microscope (Nikon) coupled to a Tsunami Dye Sapphire Laser (Spectra Physics). Samples images were recorded in fluid (medium growth) at room temperature. These results are shown in FIG. 3A–C. Accumulation of luminescent particles on the membrane and inside the cells was observed over a period of 30 min at room temperature (FIG. 3A). Optical sectioning of cells after 15 minutes incubation with nanoparticles is shown in FIGS. 3B and 3C. The arrows indicate localized accumulation of the nanoparticles on surface and inside the cells, suggesting the intracellular penetration of the nanoparticles. Such an accumulation was not observed with LHRH-negative nanoparticle studies or LHRH positive nanoparticle incubated with LHRH receptor negative cells.

These studies demonstrated the time dependent uptake of the LHRH positive nanoparticles by LHRH receptor bearing cells.

EXAMPLE 4

Figure 4A:
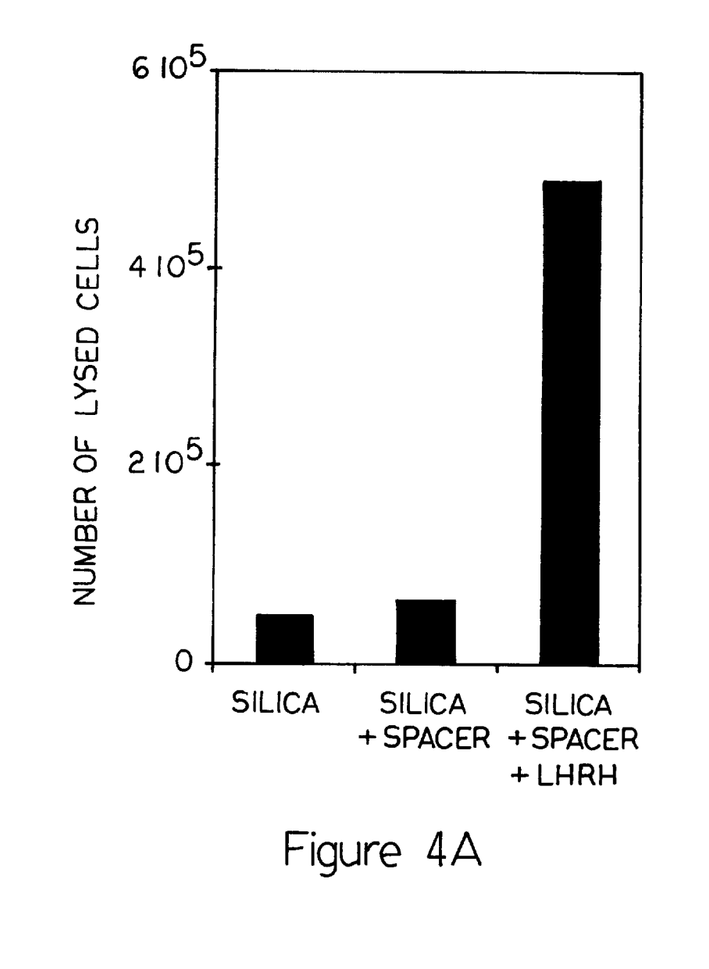
Figure 4B:
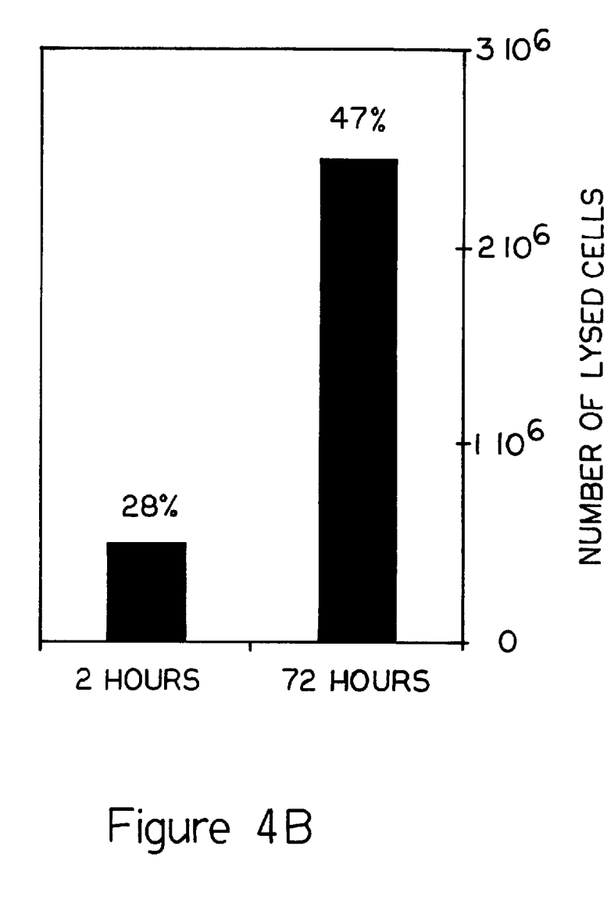

The ability of these nanoparticles to selectively affect the viability of cells, was investigated in LHRH receptor positive, MCF-7 (human breast carcinoma) and KB (oral epithelial carcinoma) and receptor negative, UCI (uterine cancer) and CV-1 (African Green monkey kidney epithelial) cell lines. Nanoparticles having LHRH on the surface (20–25 pg/1000 cells) were incubated for 2 to 72 hours at 37° C. with cell monolayers grown on 60 mm culture plates. After washing with PBS, the cells were released by trypsinization and half of the cell suspension exposed for 20 minutes (at room temperature) to a 7 Tesla magnetic field. Final cell counts revealed a 30 to 65%. loss in cell number depending on conditions. Initial results showed that the number of cells lysed by LHRH coated nanoparticles was 8 times higher than LHRH-negative nanoparticles (FIG. 4A). Incubation of the cells for 72 hours resulted a 5 fold increase in the number of lysed cells compared to the 2 hour incubation (FIG. 4B). A linear dependence of the number of lysed cells over magnetic field exposure time (up to 40 minutes) and nanoparticle concentration (0.2, 2.0, 20, and 40 pg/1000 cells) was observed.

Figure 4C:
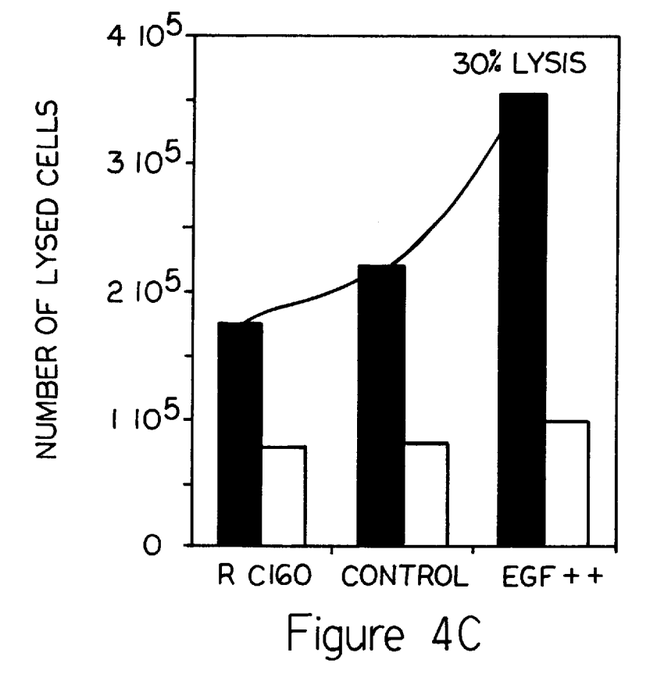

To determine the role of LHRH receptor in magnetocytolysis, the cell surface receptors were up and down regulated using Epidermal Growth Factor (EGF) and an analog of Somatostatin (RC160) treatment respectively. EGF has been shown to upregulate the LHRH receptor through activation of a tyrosine kinase which activates the receptor by phosphorylation. RC160 activates tyrosine phosphatase, which dephosphorylates the receptor, thereby deactivating it. Adherent cells were preincubated for 2 hours at 37° C. with 1 nM EGF or RC160 prior to addition of nanoparticles. FIG. 4C shows that EGF treated cells had a 2-fold increase in cell lysis compared to control (no treatment). RC160 down regulation of the LHRH receptor resulted in a 2.5-fold reduction in the lytic effect of LHRH positive particles. No change in magnetocytolysis of EGF and RC160 treatment of MCF 7 cells compared to control (no treatment) was observed using LHRH negative nanoclinics. In addition, LHRH positive and negative nanoclinics demonstrated no magnetocytolytic effect when incubated with LHRH receptor negative cell lines UCI and CV1.

Figure 5:
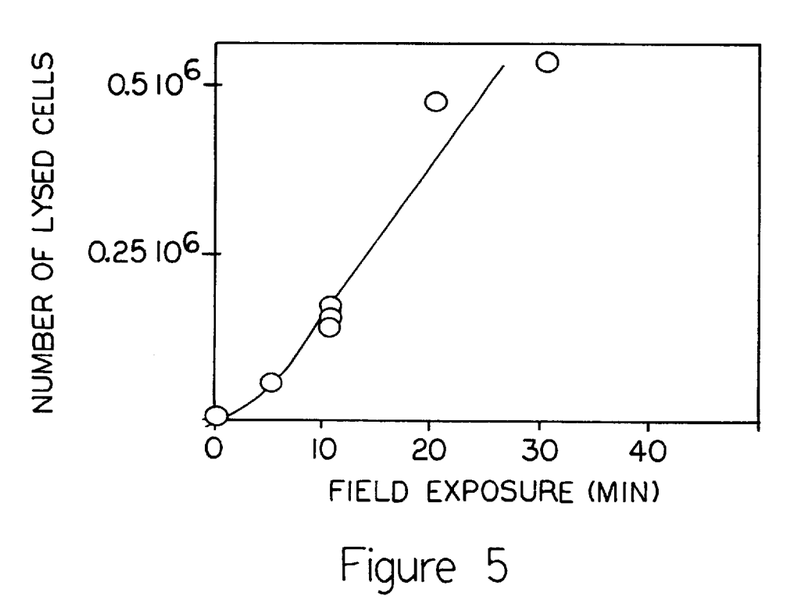
FIG. 5 is a representation of the effect of magnetic field exposure time on the lysis of cells.

To demonstrate the effect of magnetic field exposure time on the lysis of cells, MCF-7 cells were incubated 1 hour with LHRH-nanoparticles before exposure to increasing times in magnetic field. As shown in FIG. 5, the lytic effect is dependent upon the time of exposure in the magnetic field.

Further, the effect of the presence of nanoclinics in suspension with cells was investigated. MCF-7 and UCI cells were released from culture plates by trypsinization or cell scrapping. The cells were resuspended in culture media containing the nanoclinics. After incubation, the nanoclinic-cell suspension was exposed to the magnetic field and magnetocytolysis was determined. LHRH positive nanoclinics showed a greater magnetocytolytic effect on both MCF-7 and KB cells than UCI cells. LHRH negative nanoclinics had almost no lytic activity on any of the above cells. While not intending to be bound by any particular theory, these data indicate that an intimate cell-nanoclinic interaction occur in order to have a magnetocytolytic effect. The combined data from these experiments suggests that the LHRH receptors play an important role in the magnetocytolysis with this nanoclinic design.

Figure 6:
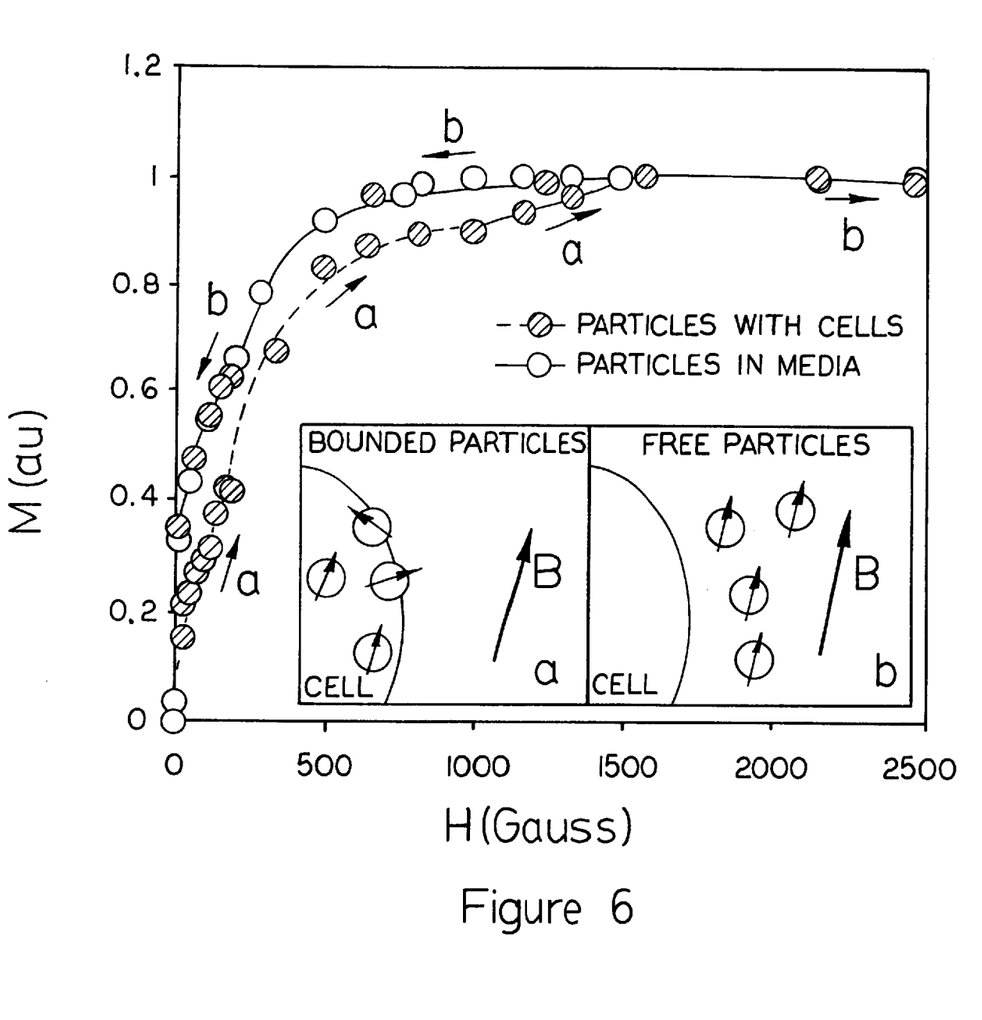
FIG. 6 is a representation of the comparison of magnetization curves of LHRH nanoclinics dispersed in cell growth medium (open circles) or incubated at 37 C. with adherent cell culture for two hours (closed circles). A resistance to magnetization is observed when the field increases (a). For higher magnetic field, the particles follow the same behavior as the isolated particles in solution (b), suggesting a physical disruption of the membrane.

To understand the mechanism of cellular disruption by magnetocytolysis, the magnetic behaviors of particles was investigated (in the presence and absence of KB cells) in the superparamagnetic (paramagnetic state for magnetic monodomain particles) range using magnetometer (SQUID). FIG. 6 shows a comparison of magnetization curves of LHRH positive particles in the presence and absence of suspended KB cells. Magnetization (M) can be described as integral of Langevin function taking into account the size polydispersity of the magnetic core. When the field is increased the magnetic moments are progressively oriented in the field which increases the magnetization (M). A plateau is reached (saturation magnetization Ms) when all the particles are oriented following the easy axis magnetization. For nanoclinics dispersed in cell growth medium, a usual curve is observed and magnetization can be fit with the Langevin equation using a 17 nm magnetic diameter with a polydispersity. For increasing magnetic field, particles incubated two hours with cells exhibit an unusual curve different from the particles without cells. No single Langevin can be used in this case to fit the curve. This can be explained in term of resistance to magnetization, which can only be induced by the cell nanoclinic interaction. This disparity was not observed in a similar experiment using LHRH negative nanoclinics. If it is considered that these nanoclinics are bound to the cell membrane or inside the cell, physical orientation in a magnetic field would predictably be harder than for free nanoclinics. As the magnetic field increases, the two curves converge. When the two curves reached the same plateau and the field is decreased the resultant curves are equivalent. At this stage all the nanoclinics can be considered as free particles. While not intending to be bound by any particular theory, this data suggest that a probable mechanism for magnetocytolysis could be a physical orientation of magnetic particles in the field, which induces a physical disruption of the cell. These data clearly shows that nanoclinics can be synthesized to selectively affect specific cell types with a controllable efficiency. The data also demonstrated the magnetocytolytic ability (cell lysing) of these nanoclinics and that this effect requires direct contact with and/or internalization into the target cell. As demonstrated here, magnetocytolytic activity was effective only in those cells capable of interacting with these nanoparticles. Evidence presented here suggests these nanoclinics enter cells by receptor mediated endocytotic process.

The foregoing description of the specific embodiments is for the purpose of illustration and is not to be construed as restrictive. From the teachings of the present invention, those skilled in the art will recognize that the device may be modified without departing from the spirit of the invention.

We claim:

1. A nanoparticle comprising:
   a) a core comprising magnetic material selected from the group consisting of ferrous oxide and ferric oxide;
   b) a silica shell surrounding the core, wherein the outer diameter of the silica shell is less than 100 nm; and
   c) a targeting agent having specific affinity for a molecule on the surface of a target cell, wherein the targeting agent is attached to the surface of the silica shell via a carbon spacer,
   wherein the nanoparticles bind to the target cell via the targeting agent and subsequently are internalized into the target cell.

2. The nanoparticle of claim 1, wherein the outer diameter of the silica shell is between 5 nm and 40 nm.

3. The nanoparticle of claim 2, wherein the outer diameter of the silica shell is about 20 nm.

4. The nanoparticle of claim 1, wherein the magnetic material is ferrous oxide.

5. The nanoparticle of claim 1, wherein the magnetic material is ferric oxide.

6. The nanoparticle of claim 1, wherein the targeting agent is a peptide or polypeptide.

7. The nanoparticle of claim 6, wherein the targeting agent is leutinizing hormone releasing hormone.

8. The nanoparticle of claim 1, wherein the spacer contains between 6 and 20 carbon atoms.

9. The nanoparticle of claim 8, wherein the spacer contains 14 carbon atoms.

10. The nanoparticle of claim 1, further comprising a tracking agent, wherein the tracking agent is attached to the magnetic material.

11. A method of causing lysis of a targeted cell comprising the steps of:
    (a) contacting nanoparticles of claim 1 with targeted cells for a time sufficient to bind and internalize the nanoparticles; wherein the targeted cells have surface molecules having specific affinity for the targeting agent, and
    (b) exposing the cells to a DC magnetic field,
    wherein said exposure causes lysis of the targeted cells which have bound and internalized the nanoparticles.

12. The method of claim 11, wherein the targeted cells express leutinizing hormone releasing hormone receptors on the cell surface.

13. The method of claim 11, wherein the magnetic core comprises ferrous oxide.

14. The method of claim 11, wherein the magnetic core comprises ferric oxide.

15. The method of claim 11, wherein the outer diameter of the silica shell is about 20 nm.

16. The method of claim 11, wherein the carbon spacer contains between 6 and 20 carbon atoms.

17. The method of claim 11, wherein the carbon spacer contains 14 carbon atoms.

18. The method of claim 11, wherein the targeting agent is leutinizing hormone releasing hormone.

19. The method of claim 11, wherein the magnetic core is ferrous oxide, the carbon spacer contains 14 carbon atoms, the silica shell is about 20 nm, and the targeting agent is leutinizing hormone releasing hormone.

20. The method of claim 11, wherein the targeted cells are selected from the group consisting of breast tumor cells, ovarian tumor cells, endometrial tumor cells, prostate tumor cells and pancreatic tumor cells.

21. A method of preparing nanoparticles of claim 1, comprising the steps of:
    a) forming magnetic core selected from the group consisting of ferrous oxide and ferric oxide;
    b) forming a silica shell around the core; and
    c) attaching a targeting agent to the silica shell via a carbon spacer,
    wherein the carbon spacer has between 6 and 20 carbon atoms, and wherein the outer diameter of the silica shell is less than 100 nm.

* * * * *